(12) United States Patent
Shimizu et al.

(10) Patent No.: US 7,202,228 B2
(45) Date of Patent: Apr. 10, 2007

(54) HYDROGELATION AGENTS

(75) Inventors: Toshimi Shimizu, Ibaraki (JP); Rika Iwamura, Ibaraki (JP); Mitsutoshi Masuda, Ibaraki (JP)

(73) Assignees: Japan Science and Technology Agency, Saitama (JP); National Institute of Advance Industrial Science and Technology, Tokyo (JP)

( * ) Notice: Subject to any disclaimer, the term of this patent is extended or adjusted under 35 U.S.C. 154(b) by 345 days.

(21) Appl. No.: 10/415,730

(22) PCT Filed: Mar. 15, 2002

(86) PCT No.: PCT/JP02/02462

§ 371 (c)(1),
(2), (4) Date: Apr. 30, 2003

(87) PCT Pub. No.: WO03/016423

PCT Pub. Date: Feb. 27, 2003

(65) Prior Publication Data

US 2004/0043951 A1    Mar. 4, 2004

(30) Foreign Application Priority Data

Aug. 20, 2001 (JP) ............................ 2001-248636

(51) Int. Cl.
*A61K 48/00* (2006.01)
*C07H 21/04* (2006.01)

(52) U.S. Cl. ........................................ 514/44; 536/23.1

(58) Field of Classification Search ............... 536/22.1, 536/25.1, 25.34, 25.6, 26.1, 23.1; 514/44
See application file for complete search history.

(56) References Cited

U.S. PATENT DOCUMENTS

| 4,271,153 A | 6/1981 | Gauri |
| 4,882,316 A | 11/1989 | Lambert et al. |
| 5,405,987 A | 4/1995 | Elango et al. |
| 5,808,067 A | 9/1998 | Saukaitis et al. |

FOREIGN PATENT DOCUMENTS

| JP | 57/106606 A2 | 7/1982 |
| JP | 8/325288 | 12/1996 |
| JP | 11/323309 A2 | 11/1999 |
| JP | 2002/248258 | 9/2000 |

OTHER PUBLICATIONS

Kabanov et al., FEBS, vol. 259(2), pp. 327-330.*
Kabanov, A.V. et al, FEBS Letters, 1990, 259(2), 327-330.*
Napoli et al, Tetrahedron, 1999, 55, 9899-9914.*
Murata et al., "Thermal and Light Control of the Sol-Gel Phase Transitin in Cholesterol-Based Organic Gels . . . ", J. Am. Chem. Soc., 1994, 116, 6664-6676.
Jeong et al., "Dual-component cholesterol-based gelators bearing complementary hydrogen-bonding sites", Supramolecular Science 3 (1996) 83-86.
Shinkai et al., "Cholesterol-based functiona tectons as versitile building-blocks for liquid crystals, organic gels and monolayers", J. Mater. Chem., 1998, 8 (3), 485-495.
Yoza, et al., "Sugar-Integrated Gelators of Organic Solvents—Their Remarkable Diversity in Gelation Ability and Aggregate Structure", Chem. Eur. J. 1999, 5, 2722-2729.
Wang et al., "Direct Observation of Sol-Gel Conversion: The Role of the Solvent in Organogel Formation", J. Am. Chem. Soc, 2000, 122, 2399-2400.
Duncan et al., "1H NMR Investigation of the Composition, Structure, and Dynamics of Cholesterol-Stilbene Tethered Dyad Organogels", Langmuir 2000, 16, 6445-6452.
Geiger et al., "Organogels Resulting from Competing Self-Assembly Units in the Gelator . . . ", Langmuir 1999, 15, 2241-2245.
Terech et al., "Low Molecular Mass of Organic Liquids and the Properties of Their Gels", Chem. Rev. 1997, 97, 3133-3159.
Ostuni et al., "Novel X-ray Method for In Situ Determination of Gelator Strand Structure: Polymorphism . . . ", Angew. Chem. Int. Ed. Engl 1996, 35 (12) 1324-1326.
Terech et al., "Structures of Organogels Based upon Cholesteryl 4-(2-Anthryloxy)butanoate . . . ", J. Phys. Chem, 1995, 99, 9558-9566.
Abdallah et al., "Organogels and Low Molecular Mass Organic Gelators", Adv. Mater. 2000, 12, 1237-1247.
Hanabusa et al., "Prominent Gelation and Chiral Aggregation of Alkylamides Derived from trans-1,2-Diaminocyclohexane", Angew. Chem. Int. Ed. Engl. 1996, 35 (17), 1949-1951.
De Loos et al., "Remarkable Stabilization of Self-Assembled Organogels by Polymerization", J. Am. Chem. Soc. 1997, 119, 12675-12676.
Schoonbeek et al., "Geminal Bis-ureas as Gelators for Organic Solvents: Gelation Properties and Structural Studies in Solution and the Gel State", Chem Eur. J. 2000, 6 (14), 2633-2643.
Carr et al., "The Design of Organic Gelators: Solution and Solid State Properties of a Family of Bis-Ureas", Tetrahedron Letters 39 (1998) 7447-7450.
Shi et al.,, "The Gelation of CO2: A Sustainable Route to the Creation of Microcellular Materials", Science 289 (1999) 1540-1544.
Fuhrhop et al., "The Chiral Bilayer Effect Stabilizes Micellar Fibers", J. Am Chem. Soc. 1987, 109, 3387-3390.

(Continued)

*Primary Examiner*—Shaojia Anna Jiang
*Assistant Examiner*—Ganapathy Krishnan
(74) *Attorney, Agent, or Firm*—Gary C. Cohn PLLC

(57) ABSTRACT

A gelatinizer is provided having a component which promises to have biological compatibility, which can easily be mass-produced by a simple method, and which can solidify a large amount of water or aqueous solution when only a very small weight of it is used.

This invention is a hydrogelatinizer represented by the general formula:

$$R-A_n$$

where A, which may be identical or different, are respectively nucleotides, n is 2 or 3, and R is a hydrocarbon chain (when n is 2, R is bivalent, and when n is 3, R is trivalent), said hydrocarbon being bonded to a phosphoric acid part of said nucleotides.

20 Claims, 1 Drawing Sheet

OTHER PUBLICATIONS

Fuhrhop et al., Stereochemistry and Curvature Effects in Supramolecular Organization and Separation Processes of Micellular N-Alkylaldonamide Mixtures, J. Am Chem. Soc. 1990, 112, 1768-1776.

Yoza et al., "Sugar-integrated gelators of organic fluids: on their versatility as building-blocks and diversity in superstructures", Chem Commun. 1998, 907-908.

Menger et al., "Anatomy of a Gel, Amino Acid Derivatives that Rigidify Water and Submillimolar Concentration", J. Am. Chem. Soc., 2000, 122, 11679-11691.

Hanabusa et al., "Formation of physical hydrogels with terpyridine-containing carboxylic acids", Colloids and Surfaces A: Physicochemical and Engineering Aspects 169 (2000) 307-315.

John et al., "Nanotube Formation from Renewable Resources via Coiled Nanofibers", Adv. Mater. 2001, 13 (10) 715-718.

Masuda et al., "Polymerization in Nanometer-Sized Fibers: Molecular Packing Order and Polymerizability", Macromolecules 2000, 33, 9233-9238.

Nakazawa et al., Spontaneous Formation of Helically Twisted Fibers from 2-Glucosamide Bolaamphiphiles . . . : Langmuir 1999, 15, 4757-4764.

Shimizu et al., "Stereochemical Effect of Even-Odd Connecting Links on Supramolecular Assemblies Made of 1-Glucosamide Bolaamphiphiles", J. Am. Chem. Soc. 1997, 119, 2812-2818.

Van Esch et al., "New Functional Materials Based on Self-Assembling Organogels: From Serendipity towards Design", Angew. Chem. Int. Ed. 2000, 30 (13) 2263-2266.

James et al., "Chiral Discrimination of Monosaccharides through Gel Formation", Chemistry Letters (1994) 273-276.

Estroff et al., "Effective Gelation of Water Using a Series of Bis-urea Dicarboxylic Acids", Angew. Chem. Int. Ed. 2000, 39, 3447-3450.

* cited by examiner

HYDROGELATION AGENTS

FIELD OF THE INVENTION

This invention relates to a hydrogelatinizer comprising a nucleotide which is a component monomer of DNA, which can solidify 500 times or more its own weight of an aqueous solution using a very small amount of a nucleotide lipid wherein this nucleotide component is connected by a hydrocarbon chain, and to a method of manufacturing this hydrogelatinizer.

DESCRIPTION OF THE RELATED ART

Hydrogels using polymer gelatinizers such as polyacrylic acid are known in the related art. However, hydrogels produced by these polymer gelatinizers are referred to as irreversible physical gels which, once formed, do not revert to the original water. The physical properties of the resulting gel such as its hardness and thermal stability cannot be controlled, and these gelatinizers furthermore have no effect on liquids containing hydrophilic organic solvents such as alcohol.

There are very few low molecular weight hydrogelatinizers, examples being long chain dicarboxylic acids and bisurea (e.g., L. A. Estroff and A. D. Hamilton, Angew.Chem.Int.Ed., 39, 3447–3450 (2000); F. M. Menger and K. L. Caran, J.Am.Chem.Soc.,122,11679–11691 (2000)).

However, when these related art hydrogels are used as biological compatibility materials, or as gel materials for separating proteins or DNA, their reactivity and toxicity were a problem.

Problems Which this Invention Aims to Solve

This invention aims to provide a gelatinizer having a component which promises to have biological compatibility, which can easily be mass-produced by a simple method, and which can solidify a large amount of water or aqueous solution when only a very small weight of it is used.

Means to Solve the Above Problems

The Inventors carried out detailed studies of methods for manufacturing hydrogelatinizers comprising effective biological material components. As a result of the studies, they discovered that a hydrogel could be manufactured having a nucleotide which is an important component monomer of genetic DNA at the end of the molecule. They further discovered that, by dissolving a nucleotide lipid wherein these (components) are connected by hydrocarbon chains in an aqueous solution, heating, and allowing to stand, water could be solidified with an extremely small component ratio, and based on this discovery, they arrived at the present invention.

The present invention is therefore a hydrogelatinizer represented by the general formula:

$R-A_n$ where A, which may be identical or different, are respectively nucleotides, n is 2 or 3, and R is a hydrocarbon chain (when n is 2, R is bivalent, and when n is 3, R is trivalent), said hydrocarbon being bonded to a phosphoric acid part of said nucleotides.

Further, the invention is a hydrogelatinizer represented by the general formula:

B—R—C where, B and C, which may be identical or different, are respectively nucleotides and R is a bivalent hydrocarbon chain, said hydrocarbon being bonded to a phosphoric acid part of said nucleotides.

The nucleotide may be monophosphoric acid, the number of carbon atoms in R may be 12–20, and the nucleotide may be 2'-deoxythymidine-3'-monophosphoric acid.

The invention is also a method of manufacturing the hydrogelatinizer according to any of claims 1–4, which comprises the steps of 1) reacting a nucleotide, comprising a sugar part protected by an acetyl group, 5'-O-4,4',4"-tris(4-benzoyloxy)trityl group or dimethoxytrityl group, with a diol or triol to produce a phosphite ester,
2) oxidizing this phosphite ester with iodine or t-butyl hydroperoxide to produce a phosphate ester, and
3) removing the protective group by using an acid.

DETAILED DESCRIPTION OF THE INVENTION

Figure 1:
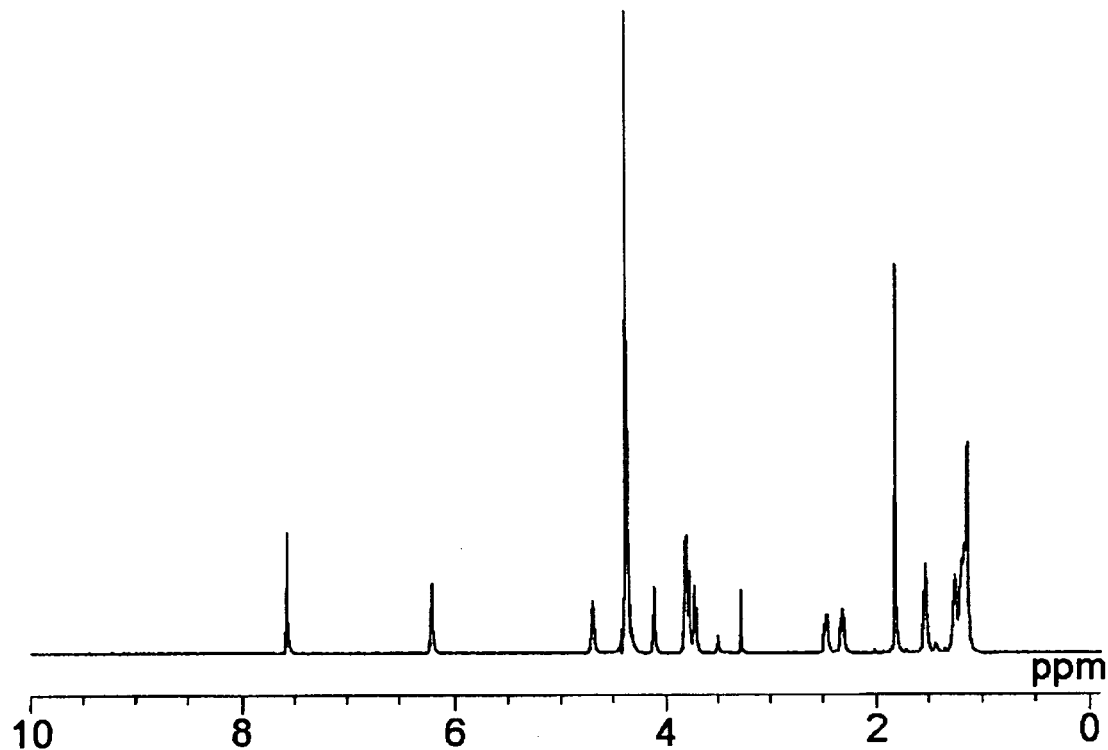
FIG. 1 is a diagram showing a $^1$H-NMR spectral chart of 1,12-(dodecanedioxy)bis(3'-phosphatidyl-2'-deoxythymidine) obtained in the Manufacturing Example 1.

The gelatinizer of this invention is represented by the following general formula:

$R-A_n$ where n is 2 or 3, but preferably 2.

A is a nucleotide of which n are present in one molecule of the gelatinizer. These nucleotides may be identical or different. The nucleotide may be a ribonucleotide or a deoxyribonucleotide, and the molecule may contain one, two or more thereof at positions 3 or 5. From the viewpoint of ease of manufacture of the gelatinizer of this invention, phosphoric acid is preferably bonded at position 3 of the deoxythymidine. As the solubility in water of the gelatinizer increases when these phosphoric acid units increase, although there is a balance with the size of the hydrophobic hydrocarbon chain, the gel tends to be more difficult to produce if the solubility of the gelatinizer in water is too high. Therefore, the number of phosphoric acid units is preferably small, and diphosphoric acid or more preferably monophosphoric acid is preferred to triphosphoric acid.

R is a hydrocarbon chain. When n is 2, the hydrocarbon chain is bivalent, and when n is 3, the hydrocarbon chain is trivalent. This hydrocarbon chain has the function of imparting hydrophobic properties to the gelatinizer, and due to the balance with the aforesaid hydrophilic phosphoric acid, it confers a gelatinizing ability on the gelatinizer. Therefore, there is no particular limitation on the hydrocarbon, which may be straight chain, branched or cyclic. Further, the bonding sites (or bonding hands) (when n=2, two sites, and when n=3, three sites) locate preferably at the end of the hydrocarbon chain.

The number of carbon atoms in this hydrocarbon chain is preferably 12–20, but more preferably 18–20. It is preferred that this hydrocarbon chain is an oligomethylene group, and in particular —$(CH_2)_m$— (m is preferably 12–20, more preferably 18–20) having the bonding sites at the end.

In this gelatinizing molecule, the hydrocarbon chain is bonded via the phosphoric acid part of the nucleotide. When the nucleotide contains plural phosphoric acid units, the nucleotide may be the oligomer (hydrocarbon chain-nucleotide)$_l$ (where l is an integer).

The nucleotide is not necessarily of only one type, and two or more types may be used. Likewise, two or more types of the hydrocarbon chain may be used.

A specific example of this gelatinizer is the gelatinizer represented by the following formula:

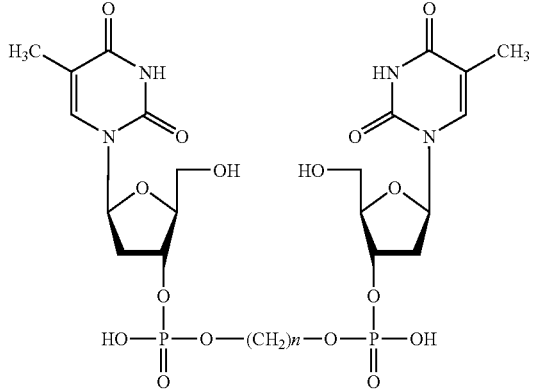

(in the formula, n is 12–20). Of these, it is preferred that n is 18 or 20 as a very small amount can then solidify a large amount of water in terms of weight ratio.

The gelatinizer this invention may be manufactured by reacting a nucleotide, having a sugar part protected, with a diol or triol to produce a phosphite ester, oxidizing this phosphite ester with iodine or t-butyl hydroperoxide to produce a phosphate ester, and removing the protective group by using an acid. When this nucleotide and diol or triol are reacted, if the phosphoric acid part of the nucleotide is protected by an amidite or the like previously, the reactivity of the phosphoric acid part increases, so the target product can easily be obtained by performing an exchange reaction between this and the diol or triol.

For example, it may be manufactured by bonding a long chain diol represented by HO—$(CH_2)_n$—OH (in the formula, n is an integer in the range 12–20) with the dioxythymidine phosphoramidite represented by the following formula:

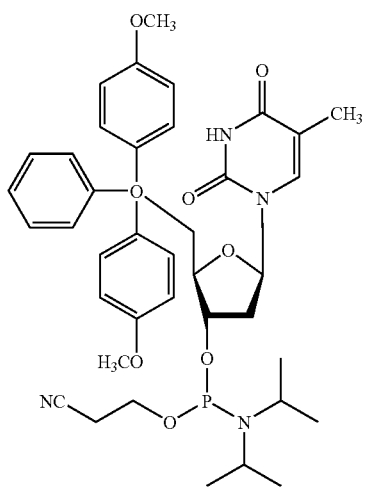

to obtain a phosphite ester, which is converted to a phosphate triester by an oxidation reaction, and finally removing the protective group.

Examples of the protective group of the sugar part of the nucleotide are acetyl, 5'-O-4,4',4"-tri (4-benzoyloxy)trityl and dimethoxytrityl, but dimethoxytrityl can efficiently and easily be removed, and is therefore convenient. For the oxidation reaction, iodine or t-butyl hydroperoxide may be used, but t-butyl hydroperoxide is preferred from the viewpoint of purification. Examples of reagents used to remove the dimethoxytrityl protective group are acetic acid, phosphoric acid, hydrochloric acid, trichloroacetic acid and trifluoroacetic acid, but trifluoroacetic acid is preferred from the viewpoint of yield.

Next, the method of manufacturing a hydrogel will be described. The gelatinizer of the invention is dissolved in an aqueous solution. A weakly acidic (pH 4) or weakly alkaline (pH 10) aqueous solution is preferred from the viewpoint of solubility. If the pH of the aqueous solution is less than 4, all of the phosphoric acid part is protonated, and it is difficult to dissolve in water. If the pH is higher than 10, the phosphoric acid part dissociates, and remains dissociated so that the water is not solidified. After dissolving the compound in the aqueous solution with heating, it is gradually cooled to room temperature and allowed to stand. In the dissolution process, heat alone is sufficient if the compound can be completely dissolved. If necessary, the compound can be efficiently converted to a simple dispersion in an aqueous solvent by ultrasound. The heating time is of the order of 30 minutes to 2 hours, but to ensure that dissolution of the compound is complete, it is preferably one hour or more. When the aqueous solution in which the compound has been dissolved is gradually cooled in air, and left at room temperature, the aqueous solution solidifies within one day-several days, and forms a hydrogel. The formation of the gel can be confirmed by inverting a test tube containing the hydrogel and observing that the gel does not flow downwards. The fluidity of the resulting gel may be varied by adjusting the pH of the water and the concentration of the gelatinizer during manufacture. In general, the formation of the hydrogel may be observed with the naked eye, but if the microstructure of the gel is observed using an optical microscope or scanning electron microscope, it can be seen that extremely fine fibers of the order of nanometers are entangled together to form a lattice structure.

Even a very small amount of the hydrogelatinizer of this invention is able to solidify a large amount of water, and the softness, stability and water retention amount of the resulting gel can be freely varied by adjusting the manufacturing conditions when it is formed. Further, as it has no toxicity, it is particularly suitable for use as a biological compatibility material, structural or culture matrix material, or as a gel for separating biological materials such as proteins and nucleic acids. As in the case of ordinary hydrogels, it may also be used as a water retaining agent (desert greenification or cultivating plants), or a moisture absorbent (pet tray urine absorbent, physiological water absorbent). In addition, it has application as a moisturizing agent in the fine chemical industry, pharmaceuticals and cosmetics, and has great industrial value.

EXAMPLES

This invention will now be described referring to specific examples, but it should be understood that the invention is not be construed as being limited in any way thereby. The Rf value in thin layer chromatography was Rf1 when a chloroform/methanol (volume ratio 4/1) mixed solvent was used as developing solvent.

Manufacturing Example 1

2.3 g (9.4 mmol) of 1,10 decane dicarboxylic acid, 3.3 ml (28 mmol) of thionyl chloride and one drop of N,N-dimethylformamide were added to dichloroethane, and the mixture was heated under reflux for two hours. After the reaction, the acid chloride obtained by completely distilling off the solvent under reduced pressure was dissolved in tetrahydrofuran. Next, 0.5 g (13 mmol) of lithium aluminium hydride was added to the tetrahydrofuran, and the mixture kept at −50° C. After gradually dripping the aforesaid acid chloride solution into this solution, the mixture was returned to room temperature, and heated under reflux for 3 hours. Subsequently, it was stirred at room temperature for 24 hours, and ethyl acetate followed by a saturated aqueous solution of sodium sulphate was added until the bubbles disappeared. Next, the reaction solution was placed under reduced pressure to distill off the solvent, the solid obtained was suspended in chloroform and filtered, and the filtrate was distilled under reduced pressure. The solid obtained was recrystallized from a solution of hexane/ethyl acetate=2/1, and 1.5 g of 1,12-dodecane diol was obtained as a white solid (yield=74%).

0.14 g (0.7 mmol) of this 1,12 dodecane diol and 0.2 g (3 mmol) of 1H-tetrazole were dissolved in tetrahydrofuran, and 1.0 g (1.4 mmol) of 5'-O-dimethoxytrityl-2'-deoxythymidine-3'-O——[O-(2-cyanoethyl)-N,N-diisopropylphosphoramidite] was added. After stirring at room temperature for 24 hours, 0.4 ml of a 70% aqueous solution of t-hydroperoxide was added to the reaction solution, and stirred for one hour. Next, 8 ml of a 28% aqueous solution of ammonia was added and stirred for 24 hours, the solvent was distilled off under reduced pressure, and the solid obtained was purified by silica gel column chromatography (eluent: chloroform/methanol=4/1). The solid obtained was dissolved in chloroform, 0.5 ml of trifluoroacetic acid was added, and the solid which separated was rinsed with chloroform. This was re-precipitated from chloroform/methanol=1/1 solution to give 0.2 g of 1,12-(dodecanedioxy)bis(3'-phosphatidyl-2'-deoxythymidine) (Compound 1) as a white powder (yield 35%).

The $^1$H-NMR spectrum of this compound is shown in FIG. 1. In the $^1$H-NMR (heavy water, 25° C.), signals due to the methylene groups of long chain alkyl groups having a σ value of 1.2–1.3 ppm, 1.6 ppm, 3.8 ppm, and signals due to the methyl protons bonded at the 5 position of the pyrimidine base in the vicinity of 1.9 ppm, the protons bonded at the 2' position of deoxyribose in the vicinity of 2.4 and 2.6 ppm, the methylene protons bonded to the 5' position of deoxyribose in the vicinity of 3.8 ppm, the proton bonded to the 4' position of deoxyribose in the vicinity of 4.2 ppm, the proton bonded to the 3' position of deoxyribose in the vicinity of 4.8 ppm, the proton bonded to the 1' position of deoxyribose in the vicinity of 6.3 ppm, the proton bonded to the 6 position of the pyrimidine base in the vicinity of 7.7 ppm, and the imido group NH proton bonded to the 3 position of the pyrimidine base in the vicinity of 9.2 ppm, were respectively observed.

The physical properties and detailed mass spectral analysis results for this compound are as follows.

Rf value of thin layer chromatography=0.71(chloroform/methanol=1/1)

Melting point=232° C. (decomposition)

Detailed mass spectrum analysis value (as [M−H+]−), calculated value: 809.2775, experimental value: 809.2770.

Manufacturing Example 2

An identical procedure to that of Manufacturing Example 1 was performed using 1,11-undecane carboxylic acid instead of 1,10-decane dicarboxylic acid, and 1,13-(tridecanedioxy)bis-(3'-phosphatidyl-2'-deoxythymidine) (Compound 2) was obtained (yield 40%).

The physical properties and detailed mass spectral analysis results for this compound are as follows.

Rf value of thin layer chromatography=0.70(chloroform/methanol=1/1)

Melting point=225° C. (decomposition)

Detailed mass spectrum analysis value (as [M−H+]−), calculated value: 823.2932, experimental value: 823.2937.

Manufacturing Example 3

An identical procedure to that of Manufacturing Example 1 was performed using 1,12-dodecane dicarboxylic acid instead of 1,10-decane dicarboxylic acid, and 1,14-(tetradecanedioxy)bis-(3'-phosphatidyl-2'-deoxythymidine) (Compound 3) was obtained (yield 25%).

The physical properties and detailed mass spectral analysis results for this compound are as follows.

Melting point=230° C. (decomposition)

Rf value of thin layer chromatography=0.70(chloroform/methanol=1/1)

Detailed mass spectrum analysis value (as [M−H+]−), calculated value: 837.3088, experimental value: 837.3074.

Manufacturing Example 4

An identical procedure to that of Manufacturing Example 1 was performed using 1,13-tridecane dicarboxylic acid instead of 1,10-decane dicarboxylic acid, and 1,15-(pentadecanedioxy)-bis(3'-phosphatidyl-2'-deoxythymidine) (Compound 4) was obtained (yield 36%).

The physical properties and detailed mass spectral analysis results for this compound are as follows.

Rf value of thin layer chromatography=0.70(chloroform/methanol=1/1)

Melting point=232° C. (decomposition)

Detailed mass spectrum analysis value (as [M−H+]−), calculated value: 851.3245, experimental value: 851.3255.

Manufacturing Example 5

An identical procedure to that of Manufacturing Example 1 was performed using 1,14-tetradecane dicarboxylic acid instead of 1,10-decane dicarboxylic acid, and 1,16-(hexadecanedioxy)-bis(3'-phosphatidyl-2'-deoxythymidine) (Compound 5) was obtained (yield 30%).

The physical properties and detailed mass spectral analysis results of this compound are as follows.

Melting point=227° C. (decomposition)

Rf value of thin layer chromatography=0.67(chloroform/methanol=1/1)

Detailed mass spectrum analysis value (as [M−H+]−), calculated value: 865.3401, experimental value: 865.3423.

Manufacturing Example 6

An identical procedure to that of Manufacturing Example 1 was performed using 1,16-hexadecane dicarboxylic acid instead of 1,10-decane dicarboxylic acid, and 1,18-(octadecanedioxy)bis-(3'-phosphatidyl-2'-deoxythymidine) (Compound 6) was obtained (yield 20%).

The physical properties and detailed mass spectral analysis results of this compound are as follows.

Melting point=230° C. (decomposition)
Rf value of thin layer chromatography=0.62(chloroform/methanol=1/1)
Detailed mass spectrum analysis value (as [M−H+]-), calculated value: 893.3714, experimental value: 893.3719.

Manufacturing Example 7

An identical procedure to that of Manufacturing Example 1 was performed using 1,18-octadecane dicarboxylic acid instead of 1,10-decane dicarboxylic acid, and 1,20-(icosanedioxy)bis-(3'-phosphatidyl-2'-deoxythymidine) (Compound 7) was obtained (yield 36%).

The physical properties and detailed mass spectral analysis results of this compound are as follows.

Melting point=233° C. (decomposition)
Rf value of thin layer chromatography=0.60(chloroform/methanol=1/1)
Detailed mass spectrum analysis value (as [M−H+]-), calculated value: 921.4027, experimental value: 921.4022.

Example 1

100 mg of Compound 1 (1,12-(dodecanedioxy)bis(3'-phosphatidyl-2'-deoxythymidine) obtained in Manufacturing Example 1 was introduced into a sample bottle containing 0.5 ml of water, and dissolved while maintaining the temperature at 60° C. or more. After leaving the resulting aqueous solution at room temperature, the aqueous solution solidified after several days and the desired hydrogel was thus obtained.

Example 2

An identical procedure to that of Example 1 was followed using Compound 2 1,13-(tridecanedioxy)bis(3'-phosphatidyl-2'-deoxythymidine) obtained in Manufacturing Example 2, and a hydrogel was obtained.

Example 3

Figure 2:
FIG. 2 is a diagram showing a scanning electron micrograph of a freeze-dried hydrogel of Example 3.

1 mg of Compound 7 (1,20-(icosanedioxy)bis(3'-phosphatidyl-2'-deoxythymidine) obtained in Manufacturing Example 7 was introduced into a sample bottle containing 0.5 ml of water. While maintaining the temperature at 60° C. or more, it was irradiated with ultrasound for one hour and the compound was dissolved. After leaving the resulting aqueous solution at room temperature, the aqueous solution solidified after several days and the desired hydrogel was thus obtained. A scanning electron micrograph of the freeze-dried hydrogel is shown in FIG. 2.

Examples 4–10

The gelatinizing ability was examined for aqueous solutions, of varying pH, of Compounds 1–7 synthesized in Manufacturing Examples 1–7. 10 mg of these compounds was placed in a sample bottle together with 0.5 ml of buffer solution adjusted to various pH, and while maintaining the temperature at 60° C. or more, the mixture was irradiated with ultrasound for one hour. After leaving the resulting aqueous solution at room temperature, the formation of a gel was observed. These results are shown in Table 1.

TABLE 1

| Compound | pH 168 | pH 401 | pH 755 | pH 918 | milliQ water |
|---|---|---|---|---|---|
| 1 | I | S | S | S | S |
| 2 | I | S | S | S | S |
| 3 | I | S | S | S | S |
| 4 | I | S | S | S | P |
| 5 | I | S | S | S | P |
| 6 | I | P | P | S | G |
| 7 | I | LG | G | G | G |

In the table, the formation of gel is indicated by "G", partial formation of gel is indicated by "LG", unchanged aqueous solution is indicated by "S", the formation of a precipitate is indicated by "P", and insolubility is indicated by "I".

It is seen that when the concentration of hydrogelatinizer is 2wt %, Compound 6 and Compound 7 efficiently solidified milliQ water (distilled water) or water of pH 4–9, and the desired hydrogel was obtained.

What is claimed is:

1. A hydrogelatinizer represented by the general formula:

wherein each A is a nucleotide, which may be identical to or different from the other A group(s), n is 2 or 3, and R is a hydrocarbon chain having 12–20 carbon atoms that is bivalent when n is 2 and trivalent when n is 3, said hydrocarbon being bonded to a phosphoric acid part of said nucleotides.

2. A hydrogelatinizer represented by the general formula:

where, B and C, which may be identical or different, are respectively nucleotides and R is a bivalent hydrocarbon chain having 12–20 carbon atoms, said hydrocarbon being bonded to a phosphoric acid part of said nucleotides.

3. The hydrogelatinizer according to claim 1, wherein said nucleotide is 2'-deoxythymidine-3'-monophosphoric acid.

4. A method of manufacturing the hydrogelatinizer according to claim 1, which comprises the steps of reacting a nucleotide, comprising a sugar part protected by an acetyl group, 5'-O-4,4',4"-tris(4-benzoyloxy)trityl group or dimethoxytrityl group, with a diol or triol to produce a phosphite ester, oxidizing this phosphite ester with iodine or t-butyl hydroperoxide to produce a phosphate ester, and removing the protective group by using an acid.

5. A hydrogelatinizer according to claim 2, wherein said nucleotide contains only one phosphoric acid group.

6. A hydrogelatinizer according to claim 2, wherein said nucleotide is 2'-deoxythymidine-3'-monophosphoric acid.

7. A hydrogelatinizer according to claim 5, wherein said nucleotide is 2'-deoxythymidine-3'-monophosphoric acid.

8. A method of manufacturing the hydrogelatinizer according to claim 2, which comprises the steps of reacting a nucleotide, comprising a sugar part protected by an acetyl group, 5'-O-4,4',4"-tris(4-benzoyloxy)trityl group or dimethoxytrityl group, with a diol or triol to produce a phosphite ester, oxidizing this phosphite ester with iodine or t-butyl hydroperoxide to produce a phosphate ester, and removing the protective group by using an acid.

9. A method according to claim 4, wherein said nucleotide contains only one phosphoric acid group.

10. A method of according to claim 9, wherein said nucleotide is 2'-deoxythymidine-3'-monophosphoric acid.

11. A method according to claim 8, wherein said nucleotide contains only one phosphoric acid group.

12. A method of claim 11, wherein said nucleotide is 2'-deoxythymidine-3'-monophosphoric acid.

13. A method of manufacturing the hydrogelatinizer according to claim 1, which comprises the steps of reacting a nucleotide comprising a sugar part having a protective group and a phosphoric acid part, with a diol or triol to produce a phosphite ester, oxidizing this phosphite ester to produce a phosphate ester, and removing the protective group from the sugar part of the nucleotide.

14. The method of claim 13 wherein the phosphoric acid part of the nucleotide has a protective group.

15. The method of claim 14 wherein the phosphoric acid part of the nucleotide is protected with an amidite group.

16. A method of manufacturing the hydrogelatinizer according to claim 2, which comprises the steps of reacting a nucleotide comprising a sugar part having a protective group and a phosphoric acid part, with a diol or triol to produce a phosphite ester, oxidizing this phosphite ester to produce a phosphate ester, and removing the protective group from the sugar part of the nucleotide.

17. The method of claim 16 wherein the phosphoric acid part of the nucleotide has a protective group.

18. The method of claim 17 wherein the phosphoric acid part of the nucleotide is protected with an amidite group.

19. A hydrogel comprising water and an effective amount of the hydrogelatinizer of claim 1.

20. A hydrogel comprising water and an effective amount of the hydrogelatinizer of claim 2.

* * * * *